(12) United States Patent
Wagner

(10) Patent No.: US 6,691,770 B2
(45) Date of Patent: Feb. 17, 2004

(54) COOLING APPARATUS

(75) Inventor: Guy R. Wagner, Loveland, CO (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/164,273

(22) Filed: Jun. 5, 2002

(65) Prior Publication Data

US 2003/0102109 A1 Jun. 5, 2003

Related U.S. Application Data

(63) Continuation-in-part of application No. 10/006,412, filed on Dec. 3, 2001, now Pat. No. 6,561,261.

(51) Int. Cl.⁷ .............................................. H05K 7/20
(52) U.S. Cl. .............................. 165/104.33; 165/80.3; 165/121; 361/697
(58) Field of Search .............................. 165/80.3, 121, 165/185, 104.33; 361/697

(56) References Cited

U.S. PATENT DOCUMENTS

| | | | | |
|---|---|---|---|---|
| 2,413,179 A | * | 12/1946 | Grandmont et al. | 165/185 |
| 3,193,003 A | * | 7/1965 | McCuen | 165/185 |
| 3,566,959 A | * | 3/1971 | Koltuniak et al. | 165/80.3 |
| 5,132,780 A | * | 7/1992 | Higgins, III | 257/722 |
| 5,828,551 A | * | 10/1998 | Hoshino et al. | 361/697 |
| 5,957,659 A | * | 9/1999 | Amou et al. | 415/178 |
| 6,535,385 B2 | * | 3/2003 | Lee | 361/697 |

* cited by examiner

Primary Examiner—Allen Flanigan

(57) ABSTRACT

A heat sink comprises a core member comprising at least one core member first surface. The core member first surface is adapted to contact or be located adjacent at least a portion of the heat source. At least one outer peripheral surface is located on the core member. At least one cooling fin is operatively connected to the outer peripheral surface and extends in a direction substantially normal to the core member first surface. At least a portion of the outer peripheral surface is tapered, wherein the circumference of the outer peripheral surface in the proximity of the first surface is greater than the circumference of the outer peripheral surface not in the proximity of the first surface.

28 Claims, 15 Drawing Sheets

COOLING APPARATUS

This application is a continuation-in-part of U.S. application Ser. No. 10/006412 of Wagner filed on Dec. 3, 2001, now U.S. Pat. No. 6,561,261, which is hereby incorporated by reference for all that is disclosed therein.

FIELD OF THE INVENTION

The present invention relates generally to cooling devices.

BACKGROUND OF THE INVENTION

Electronic components, such as integrated circuits, are increasingly being used in different devices. One prevalent example of a device using integrated circuits is the computer. The central processing unit or units of most computers, including personal computers, is typically constructed from a plurality of integrated circuits. Integrated circuits are also used in other computer circuitry. For example, interface and memory circuits typically comprise several integrated circuits.

During normal operation, many electronic components, such as integrated circuits, generate significant amounts of heat. If this heat is not continuously removed, the electronic component may overheat, resulting in damage to the component and/or a reduction in its operating performance. For example, an electronic component may encounter thermal runaway, which may damage the electronic component. In order to avoid such problems caused by overheating, cooling devices are often used in conjunction with electronic components.

One such cooling device used in conjunction with electronic components is a heat sink. A heat sink is a device that draws heat from an electronic component and convects the heat to the surrounding atmosphere. The heat sink is usually placed on top of, and in physical contact with, the heat generating electronic component so as to provide thermal conductivity between the electronic component and the heat sink.

One method of increasing the cooling capacity of heat sinks is by including a plurality of cooling fins attached to the heat sink and a cooling fan that forces air past the cooling fins. The cooling fins serve to increase the surface area of the heat sink and, thus, increase the convection of heat from the heat sink to the surrounding atmosphere. The fan serves to force air past the fins, which further increases the convection of heat from the heat sink to the surrounding atmosphere. This increased convection, in turn, allows the heat sink to draw more heat from the electronic component. In this manner, the heat sink is able to draw a significant amount of heat away from the electronic component, which serves to further cool the electronic component.

Cooling fins with larger surface areas, however, tend to have significant barrier layers of air on the cooling fin surfaces when air is forced past the cooling fins. An air barrier layer is air that is adjacent the surface of a cooling fin and remains substantially stationary relative to the cooling fin as air is forced past the cooling fin. Thus, a significant barrier layer may result in the air being forced past cooling fins not being able to effectively remove heat from the cooling fins. Accordingly, increasing the area of individual cooling fins may not result in a proportional cooling capability of the heat sink.

Another problem associated with large cooling fins is that they occupy large spaces within an electronic device, which could otherwise be used to reduce the size of the electronic device. Large cooling fins also occupy space that could otherwise be used to increase the concentration of electronic components located within the electronic device. Electronic devices are becoming much smaller, thus, a reduced space or a higher concentration of electronic components within the electronic devices is beneficial. The use of large cooling fins tends to increase the size of the electronic devices or reduce the concentration of electronic components located therein.

Therefore, a device and/or method is needed to overcome some or all the aforementioned problems.

SUMMARY OF THE INVENTION

The present invention is directed toward a heat sink for removing heat from a heat source. The heat sink may comprise a core member comprising at least one core member first surface. The core member first surface is adapted to contact or be located adjacent at least a portion of the heat source. At least one outer peripheral surface is located on the core member. At least one cooling fin is operatively connected to the outer peripheral surface and extends in a direction substantially normal to the core member first surface. At least a portion of the outer peripheral surface is tapered, wherein the circumference of the outer peripheral surface in the proximity of the first surface is greater than the circumference of the outer peripheral surface not in the proximity of the first surface.

DETAILED DESCRIPTION

Figure 1:
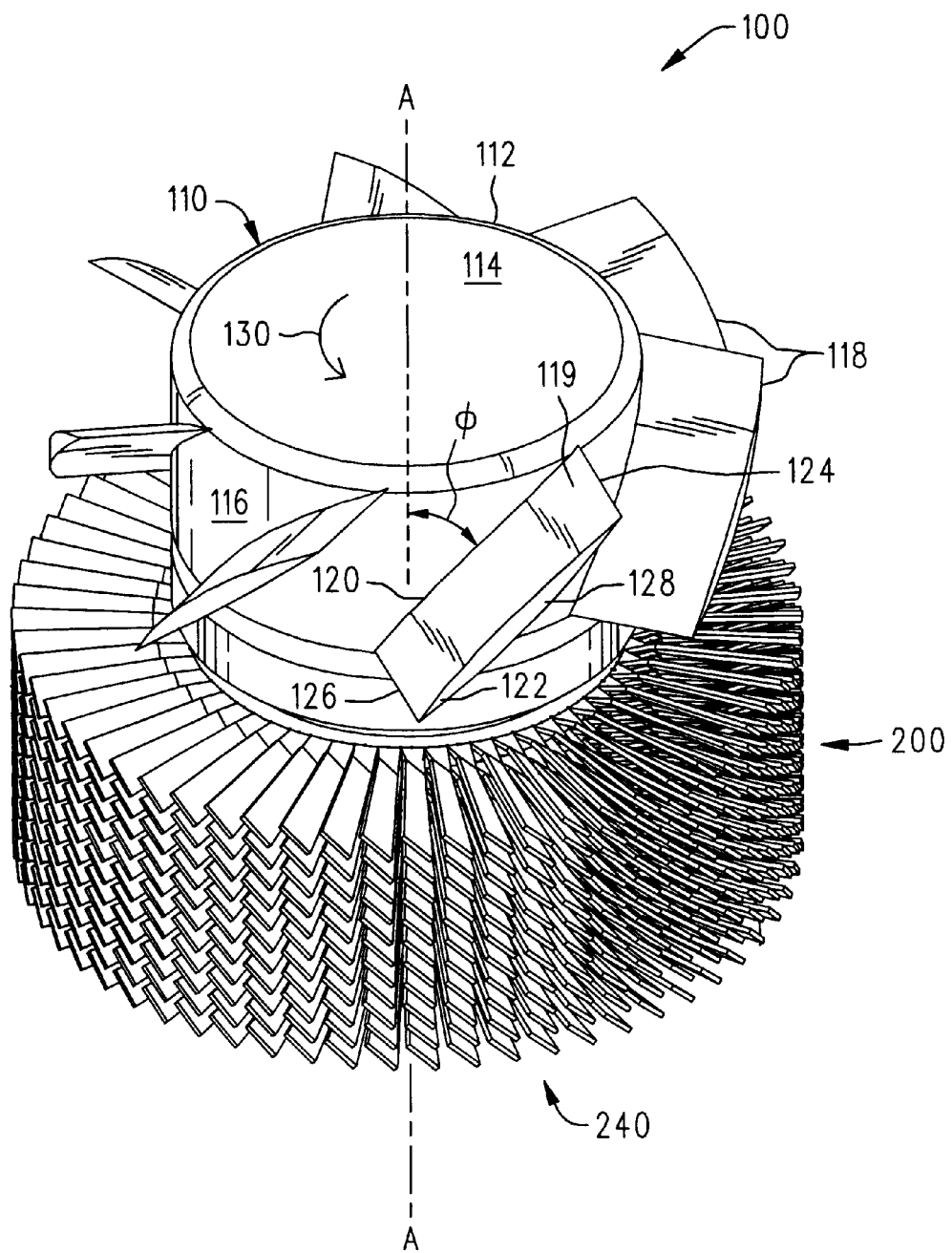
FIG. 1 is a top perspective view of a cooling device having a plurality of fin rings and a fan.

A non-limiting embodiment of a cooling device 100 is shown in FIG. 1. The cooling device 100 may have an air blowing device 110 associated with a heat sink 200. In the non-limiting embodiment described herein, the air blowing device 110 is a fan and is sometimes referred to as the fan 110. However, it is to be understood that the air blowing device 110 may be other devices, such as duct work that causes air to be blown onto the heat sink 200. The following description describes the heat sink 200 followed by a description of the fan 110. A description of the operation of the fan 110 associated with the heat sink 200 follows their individual descriptions.

Figure 2:
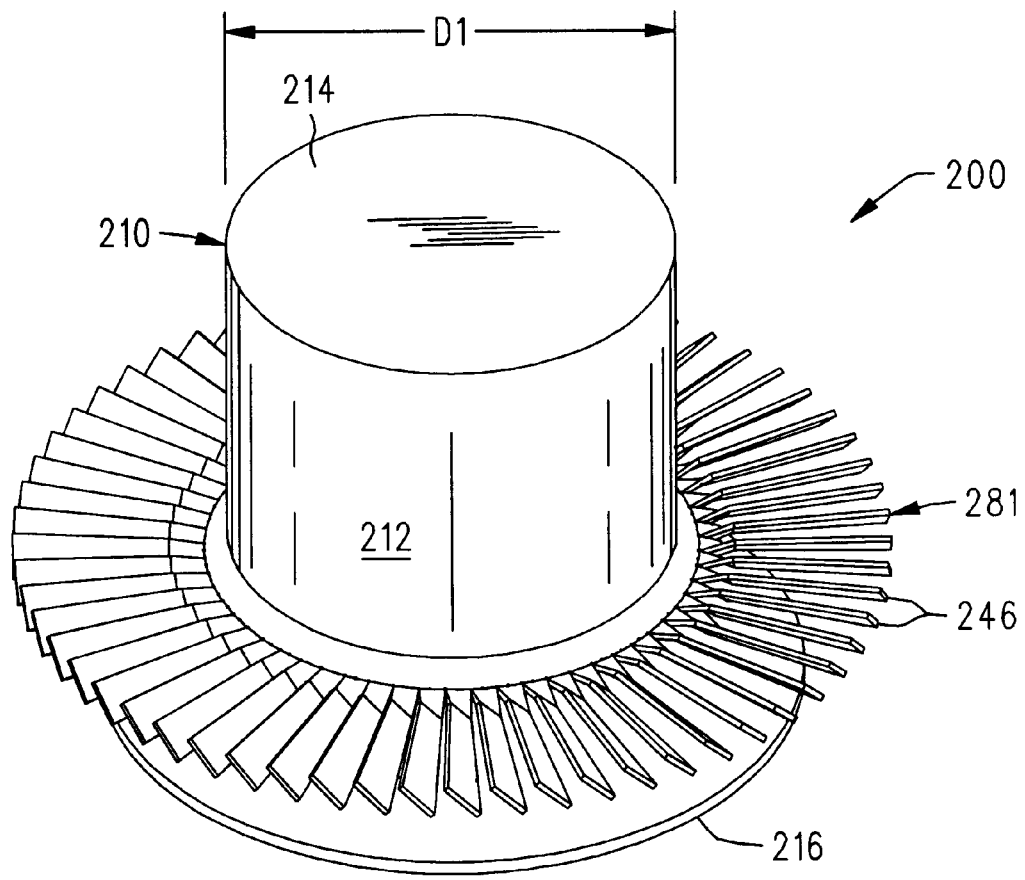
FIG. 2 is a top perspective view of the cooling device of FIG. 1 having a single first fin ring and without the fan.

Referring to FIG. 2, which shows a partially constructed heat sink 200, the heat sink 200 may have a core member 210 (sometimes referred to herein simply as the core 210) with a first fin ring 281 located adjacent the core 210. For illustration purposes, FIG. 2 shows only a single first fin ring 281 attached to or otherwise operatively associated with the core 210. Further below in this description, the heat sink 200 will be described having a plurality of fin rings 240, FIG. 1, operatively associated with the core 210. The first fin ring 281 and other fin rings described herein are sometimes referred to as cooling fin devices.

Figure 3:
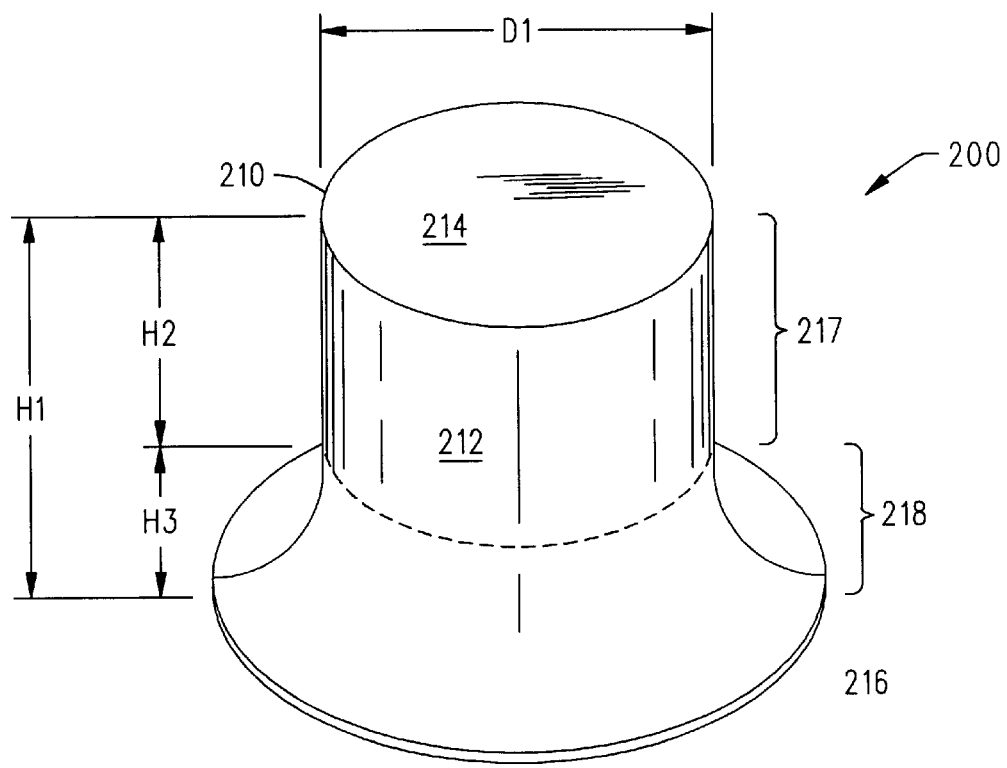
FIG. 3 is a top perspective view of the core member of the cooling device of FIG. 1.

A top perspective view of the core 210 is shown in FIG. 3. The view of FIG. 3 is similar to the core 210 of FIG. 2 without any fin rings attached thereto. The core 210 may be made of a thermally conductive material, such as copper or aluminum. The core 210 may have a top surface or portion 214 and a lower surface or portion 216. A height H1 may extend between the top portion 214 and the lower portion 216 and may, as an example, be approximately 3.0 centimeters. The top portion 214 may be substantially round and may have a diameter D1 associated therewith. The diameter D1 may, as an example, be approximately 3.0 centimeters. The diameter D1 and height H1, however, are dependent on the specific cooling application of the cooling device 100 and may vary accordingly both in size and shape.

The core 210 may have an outer peripheral surface 212 (sometimes simply referred to herein as the peripheral surface 212) located between the top portion 214 and the lower portion 216. The peripheral surface 212 of the core 210 has a cylindrical portion 217 and a tapered portion 218. It should be noted that the use of a partially cylindrical core and, thus, a cylindrical portion 217 is for illustration purposes only. The core 210 may be virtually any shape that serves to allow the fin rings to be associated therewith. For example, the core 210 and, thus, the top portion 214, may be oval. It should also be noted that the core 210 shown in FIG. 3 has a single peripheral surface 212. Other embodiments of the core 210 may have several peripheral surfaces. For example, the peripheral surface 212 may be divided into several portions or may form several surfaces.

The cylindrical portion 217 of the core 210 has a height H2 and the tapered portion 218 has a height H3. As shown in FIG. 3, the cylindrical portion 217 of the core 210 extends between the top portion 214 and a portion of the peripheral surface 212 indicated by a dashed line. The tapered portion 218 extends between the dashed line and the lower portion 216. In the embodiment described herein, the fin rings shown in FIG. 2 are attached to the cylindrical portion 217 of the core 210. As described in greater detail below, the tapered portion 218 serves to divert air from the core 210, which increases the efficiency of the heat sink 100, FIG. 1.

Figure 4:
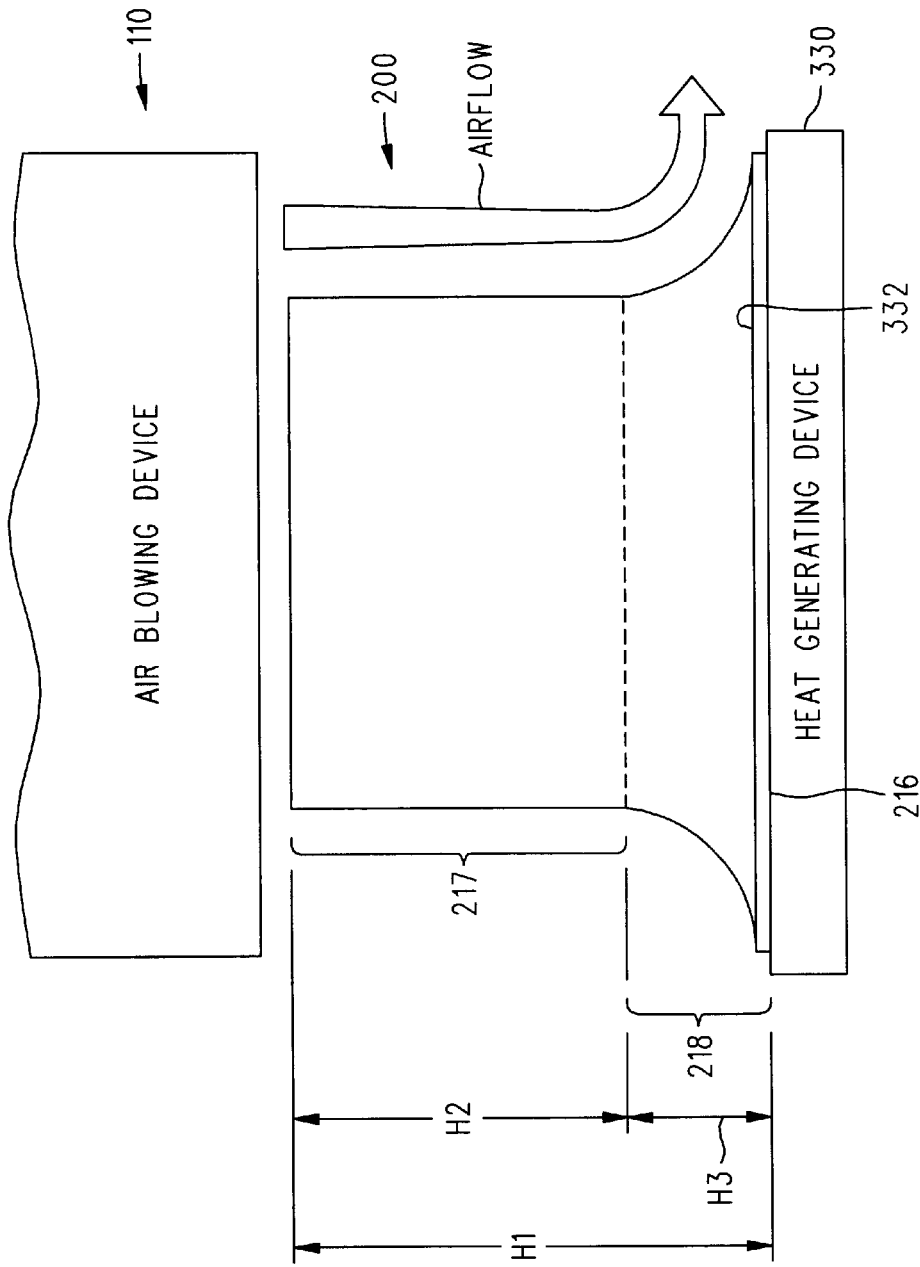
FIG. 4 is a side view of the core member of the cooling device of FIG. 1 without any fin rings associated therewith.

Referring to FIG. 4, which is a side view of the core 210 of FIG. 3, the lower portion 216 of the core 210 is adapted to be in thermal contact or physical contact with a heat generating device 330. In the embodiment described herein, the lower portion 216 of the core 210 is adapted to contact a top surface 332 of the heat generating device 330. The contact between the core 210 and the heat generating device 330 provides for the transfer of heat from the heat generating device 330 to the core 210. For example, in the situation where the heat generating device 330 is an integrated circuit, the top surface 332 of the integrated circuit is typically a planar surface. Accordingly, the lower portion 216 of the core 210 may be a substantially planar surface and may have an area that is approximately the same as or greater than the area of the top surface 332 of the heat generating device 330.

As shown in FIG. 3 and FIG. 4, the circumference or perimeter of the peripheral surface 212 of the core 210 is the greatest in the proximity of the lower portion 216 of the core 210. More specifically, the circumference of the peripheral surface 212 increases in the tapered portion 218 of the core 210 toward the lower portion 216 of the core 210. Accordingly, the circumference is at a minimum in the proximity of the cylindrical portion 217 of the core and is at a maximum in the proximity of the lower portion 216. This tapering of the core 210 causes airflow generated by the air blowing device 110 to be freely exhausted away from the lower portion 216 of the core 210 as shown in FIG. 4. As the airflow transitions from a direction toward the heat generating device 330 to a direction away from the heat generating device 330, back pressure and/or turbulence are reduced by the tapered portion 218. Therefore, a greater amount of air may pass adjacent the core 210 and may remove a greater amount of heat from the core 210. With an additional and brief reference to FIG. 1, the tapering of the core 210 enables a greater amount of air to pass the cooling fins, which in turn increases the cooling capability of the heat sink 200.

The airflow shown in FIG. 4 is parallel to the peripheral surface 212. More specifically, the airflow is shown commencing at the air blowing device 110 and extending in a substantially straight line to the tapered portion 218, where it is then terminated by being exhausted from the heat sink 200. Such an airflow may exist in a situation where the airflow generated by the air blowing device 110 extends substantially normal to the air blowing device 110. For example, this airflow may exist in a situation where the air blowing device 110 is a duct that delivers forced air from a remote location.

Figure 5:
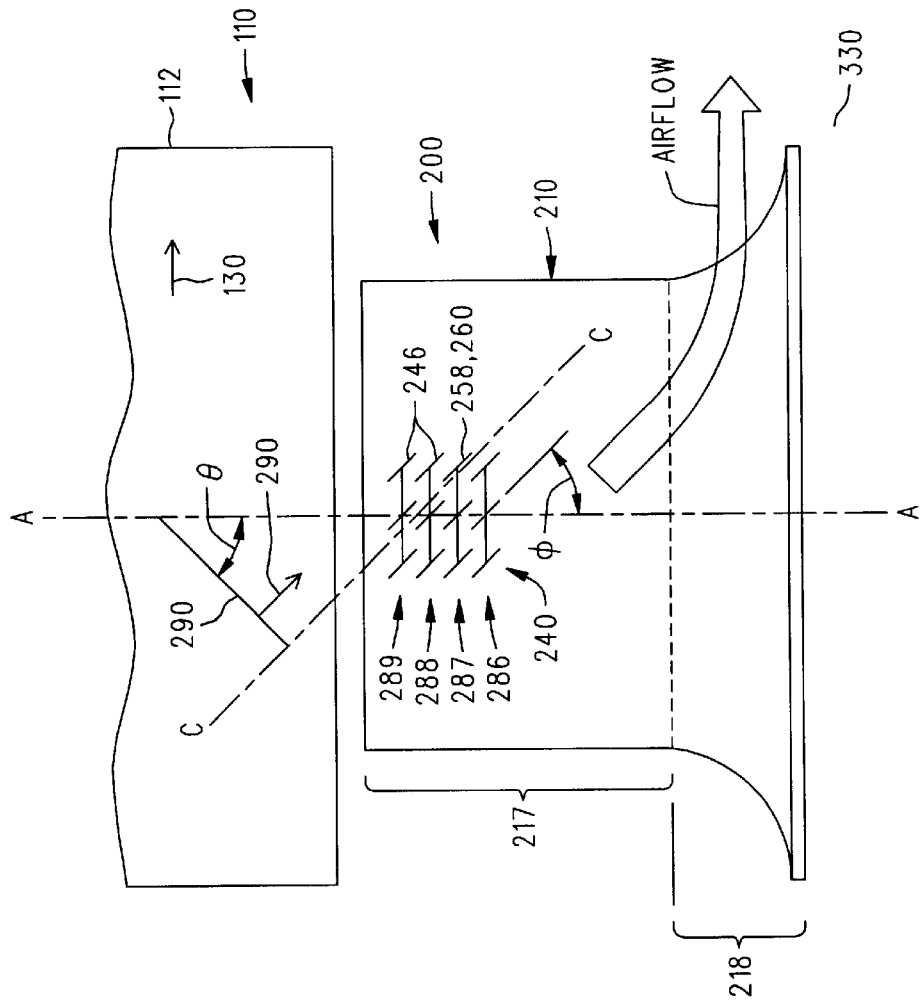
FIG. 5 is a cut away, schematic illustration of the cooling device of FIG. 1.

Referring briefly to FIG. 5, an embodiment of the cooling device 100 may have an airflow that spirals the core 210. For example, in a situation where the air blowing device 110 is a fan, the airflow may substantially spiral around the core 210 as is described in greater detail below. With additional reference to FIG. 1, the spiraling airflow shown in FIG. 5 improves the airflow associated with the fin rings as is described in greater detail below.

Referring again to FIG. 4, in the embodiment of the core 210 illustrated herein, the peripheral surface 212, including the cylindrical portion 217 and the tapered portion 218, are continuous, meaning that there are no discontinuities in the peripheral surface 212. The continuous surfaces enable the airflow shown in FIG. 4 to be less susceptible to turbulence and enables greater airflow. In another embodiment of the core 210, the peripheral surface 212 has discontinuities (not shown) and, thus, only portions of the peripheral surface 212 contact the fin rings, FIG. 2.

Figure 6:
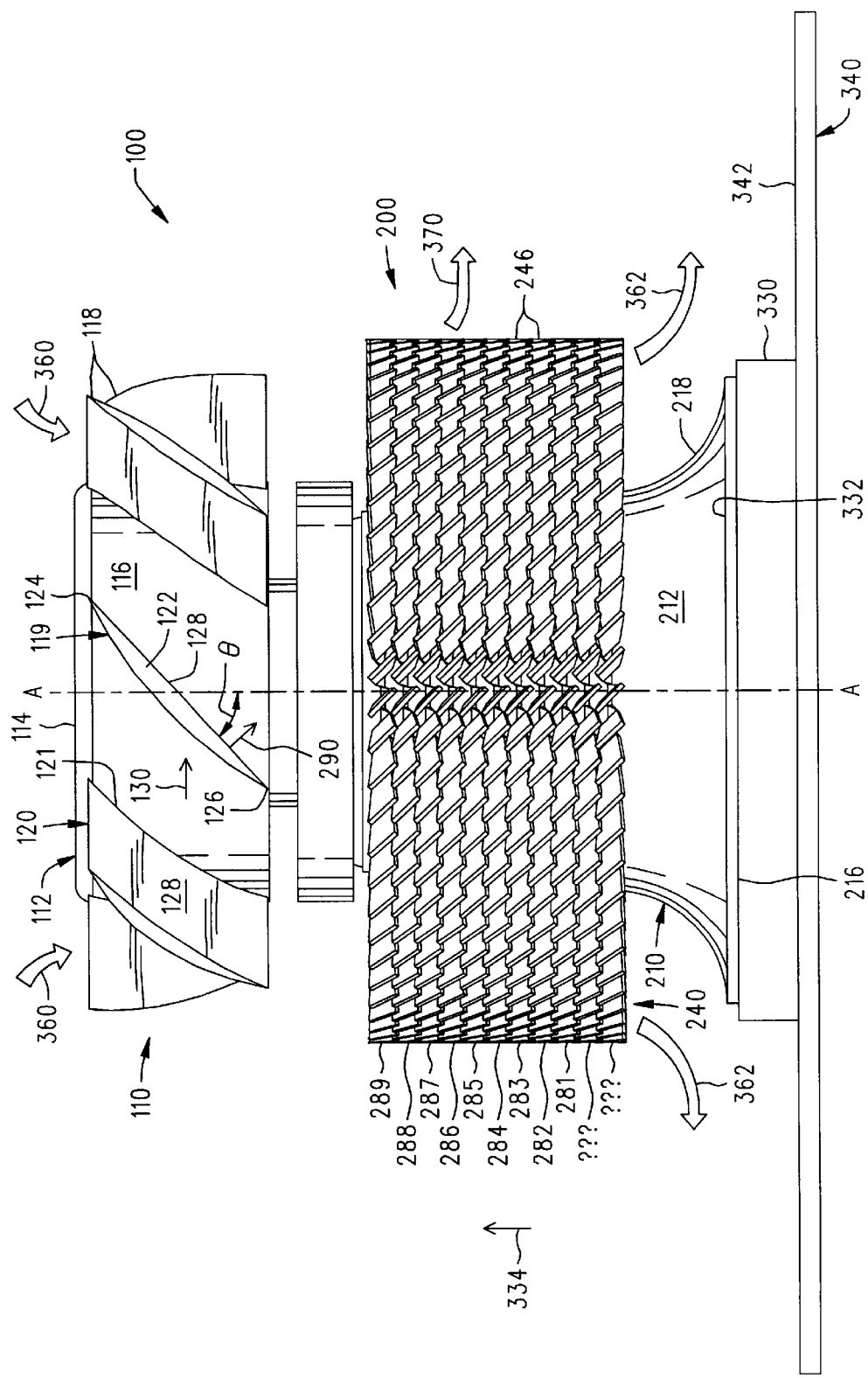
FIG. 6 is a side view of the cooling device of FIG. 1 located adjacent a heat generating electronic device.
Figure 7:
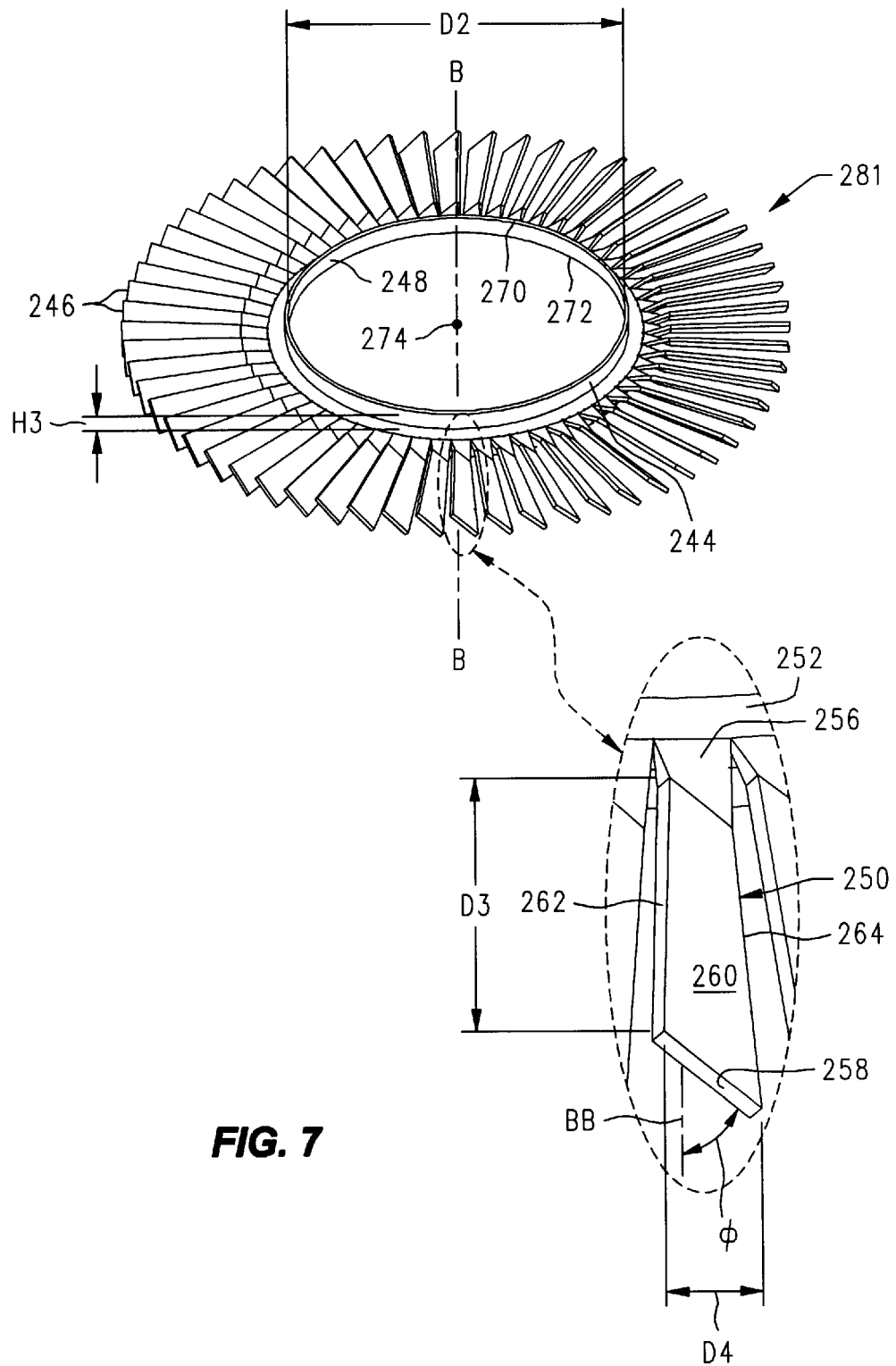
FIG. 7 is a top perspective view of a fin ring of the type illustrated in the cooling device of FIG. 2.

Having described the core 210, FIG. 2, the first fin ring 281, FIG. 7, will now be described in greater detail. FIG. 7 is a top perspective view of the first fin ring 281 separated from the core 210, FIG. 2, and is representative of the remaining fin rings 240 that may be associated with the core 210 as illustrated in FIG. 6. The first fin ring 281 may have a collar 244 with a plurality of cooling fins 246 attached thereto or otherwise associated therewith. The collar 244 may have an inner peripheral surface 248 having an upper ring portion or side 270 and a lower ring portion or side 272. The upper portion 270 and the lower portion 272 may be separated by a height H3, which may, as an example, be approximately 0.25 centimeters. The upper ring portion 270 and the lower ring portion 272 may be located on substantially parallel planes. A reference axis BB may pass through the center point 274 of a circle defined by the collar 244. The reference axis BB may be substantially normal to the planes defined by the upper ring portion 270 and the lower ring portion 272.

The inner peripheral surface 248 has a perimeter associated with it, which in the embodiment described herein is a cylindrical surface extending between the upper portion 270 and the lower portion 272. The perimeter of the inner peripheral surface 248 may be substantially similar to the perimeter of the cylindrical portion of the peripheral surface 212, FIG. 2, of the core 210. For example, the inner peripheral surface 248 may be round and may have a diameter D2 that is approximately the same or slightly smaller than the diameter D1 of the core 210, FIG. 2. In one embodiment of the heat sink 200, FIG. 2, the diameter D1 of the core 210 and the diameter D2, FIG. 7, of the first fin ring 281 are appropriately sized so as to cause an interference fit between the first fin ring 281 and the core 210 as is described in greater detail below.

The collar 244 may have an outer surface 252 wherein the cooling fins 246 are attached to the outer surface 252. Reference is made to a first fin 250, which is representative of all the cooling fins 246 and their association with the outer surface 252. The first fin 250 may have a mounting portion 256, an end portion 258, a surface 260, an upper end 262, and a lower end 264. The surface 260 may be defined by the boundaries of the mounting portion 256, the end portion 258, the upper end 262, and the lower end 264. The surface 260 may be substantially planar. A length D3 may extend between the mounting portion 256 and the end portion 258. The length D3 may, as an example, be approximately 11 to 13 millimeters. A length D4 may extend between the upper end 262 and the lower end 264. In one embodiment the length D4 is relatively small in order to reduce the boundary layer of air that may accumulate on the surface 260 of the first fin 250 when air is forced past the surface 260. The length D4 may, as an example, be approximately 3.25 millimeters. The mounting portion 256 may be a twisted portion of the first fin 250 and may serve to create an angle Φ between the end portion 258 and the reference axis BB. The angle Φ may, as an example, be approximately 45 degrees. It should be noted that the angle Φ may be determined by the direction of the airflow as shown in FIG. 4 and FIG. 5 and as described in greater detail below.

The collar 244 and the cooling fins 246 may be made of a heat conducting material such as aluminum or copper. The junction between the collar 244 and the mounting portion 256 of the cooling fins 246 may conduct heat with minimal thermal resistance. For example, the collar 244 may be integrally formed with the cooling fins 246 or they may be welded together. In a non-limiting example of manufacturing the first fin ring 281, the first fin ring 281 may be fabricated from a single metal sheet, such as a copper or aluminum sheet. The metal sheet may, as an example, have a thickness of approximately 15 to 20 thousandths of an inch. Fabrication of the first fin ring 281 may commence with stamping the collar 244 out of the metal sheet. The collar 244 is essentially a circular cutout having a diameter D2 and a height H2. Accordingly, the stamping process forms the diameter D2 and the height H2 of the collar 244. The cooling fins 246 may then be stamped out of the metal sheet. For example, the cooling fins 246 may be cut out of the metal sheet via a conventional stamping process. The metal sheet may then be placed into a dye that twists the cooling fins 246 at the mounting portion 256 in order to form the angle Φ.

Figure 8:
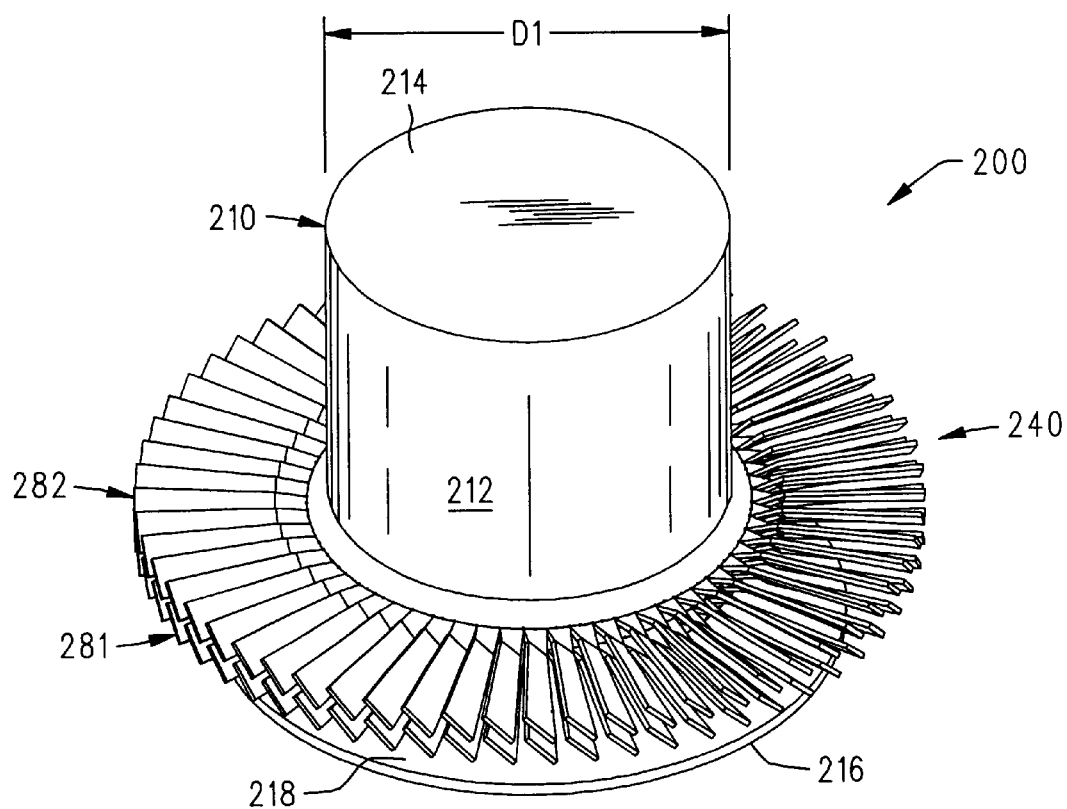
FIG. 8 is a top perspective view of the cooling device of FIG. 2 having a second fin ring located adjacent the first fin ring.

Referring again to FIG. 2 and FIG. 4, the first fin ring 281 may be pressed onto the core 210 in a conventional manner to form an interference fit between the first fin ring 281 and the core 210. The interference fit is a result of a cylindrical portion 217 of the surface 212 of the core 210 being substantially the same as the perimeter of the inner peripheral surface 248, FIG. 7, of the first fin ring 281. Accordingly, the diameter D1 of the core 210 is substantially the same or slightly larger than the diameter D2, FIG. 7, of the first fin ring 281. As shown in FIG. 2, the first fin ring 281 may be located in the vicinity of the junction of the cylindrical portion 217 and the tapered portion 218 of the core 210. Referring to FIG. 8, which is the heat sink 200 of FIG. 2 with an additional fin ring attached thereto, after the first fin ring 281 has been pressed onto the core 210 a second fin ring 282 may be pressed onto the core 210. The process of pressing fin rings 240 onto the core 210 may continue until the surface 212 of the core 210 is substantially covered with fin rings 240 as illustrated in FIG. 6.

FIG. 6 illustrates nine fin rings 240 affixed to the core 210. The fin rings 240 are referred to individually as the first through the ninth fin rings and referenced numerically as 281 through 289 respectively. The plurality of fin rings 240 substantially increases the surface area available on the heat sink 200 for convecting heat to the surrounding atmosphere. In addition, the fin rings 240 are relatively thin, which increases their ability to convect heat to the surrounding atmosphere by minimizing the air resistance through the fin rings 240 as is described below. As illustrated in FIG. 6, the cooling fins 246 are substantially planar and are located on planes that are substantially parallel to each other. As described in greater detail below, the planar arrangement of the cooling fins 246 forms channels that serve to guide air past the cooling fins 246, which increases convection of heat to the surrounding atmosphere. The planar arrangement of the fin rings 240 is described below with reference to the schematic illustration of FIG. 5.

In the embodiment of the heat sink 200 described herein, the fin rings 240 are arranged so that the cooling fins 246 are nested, meaning that they bisect airflow patterns. This nesting is illustrated in FIG. 5 between the seventh fin ring 287, the eighth fin ring 288, and the ninth fin ring 289. The cooling fins 246 of the seventh fin ring 287 and the ninth fin ring 289 are located on the same plane and thus form an air channel therebetween. This air channel is bisected by the cooling fins 246 of the eighth fin ring 288. This bisection causes some turbulence in the airflow within the cooling fins 246, which serves to break up or reduce the air barrier layer. Thus, the cooling capability of the heat sink 200 is improved. It should be noted that the nesting of the fin rings 240 enables a great number of cooling fins 246 to be associated with the heat sink 200.

Having described the heat sink 200, the fan 110 and other air blowing devices will now be described followed by a description of the association between the heat sink 200 and the fan 110.

Referring again to FIG. 6, the fan 110 may be a conventional electric fan. In other embodiments described below, the fan 110 is replaced with an air blowing device, such as duct work. The fan 110 may, as an example, be of the type commercially available from the Matsushita Electric Corporation as Model FBA06T12H and sold under the tradename PANAFLO. The fan 110 may have a rotating portion 112, wherein the rotating portion 112 may have a top portion 114, a lower portion, not shown in FIG. 6, and a peripheral side wall 116. A reference axis AA may extend through the center of the top portion 114 and may be substantially normal to the top portion 114. As described in greater detail below, the reference axis AA may define a center of rotation of the rotating portion 112. A direction 130 is used herein to describe the rotational direction of the rotating portion 112 about the reference axis AA.

The peripheral side wall 116 of the fan 110 may have a plurality of circulating fins 118 attached thereto. The circulating fins 118 may be substantially identical to each other. A first circulating fin 119 and a second circulating fin 120 are used as a reference to describe all the circulating fins 118. The circulating fins 119, 120 may have an inner side 121, an outer side 122, an upper side 124, and a lower side 126. The sides may define the boundaries of a surface 128. The inner side 121 may be attached to the peripheral side wall 116 of the rotating portion 112 in a conventional manner. For example, the circulating fins 119, 120 may be adhered to or integrally formed with the side wall 116. The attachment of the circulating fins 119, 120 to the side wall 116 may define an angle e between the surface 128 and the reference axis M. The angle $\theta$ may, as an example, be about 45 degrees. In one embodiment, the angle $\theta$ is equal to 90 degrees minus the angle $\Phi$ of FIG. 7. As described in greater detail below, the angle $\theta$ may serve to determine the direction of air flow generated by the fan 110 as the rotating portion 112 rotates in the direction 130.

Having described the fan 110 and the heat sink 200 separately, their association with each other will now be described.

As illustrated in FIG. 6, the fan 110 may be located adjacent the top portion 214, FIG. 2, of the core 210. The fan 110 may, as examples, be attached to the core 210 by the use of fasteners, e.g., screws, or it may be adhered to the core 210. It should be noted, however, that the fan 110 does not need to be physically attached to the core 210 and that the fan 110 only needs to be able to force air past the cooling fins 246.

FIG. 5, illustrates the air flow between the fan 110 and the heat sink 200 in one embodiment of the cooling device 100. It should be noted that for illustration purposes the heat sink 200 illustrated in FIG. 5 only shows a limited number of fin rings 240 and cooling fins 246. As described above, the first circulating fin 119 is positioned at an angle $\theta$ relative to the reference axis AA. In one embodiment, the angle $\theta$ is approximately forty-five degrees. The cooling fins 246 are positioned at an angle $\Phi$ relative to the reference axis AA, which, in the embodiment described herein, is approximately 45 degrees. A reference axis CC may extend parallel to the end portions 258 of the cooling fins 246 and may be substantially perpendicular to the surface 128 of the first circulating fin 119. An air flow direction 290 commences at the surface 128 of the first circulating fin 119 and extends parallel to the reference axis CC, which, in this embodiment, is normal to the surface 128. The air flow direction 290 is the direction that air flows as the first circulating fin 119 rotates in the direction 130.

When the rotating portion 112 rotates in the direction 130, the first circulating fin 119 forces air to circulate past the cooling fins 246. The airflow generated by the rotating first circulating fin 119 flows in the air flow direction 290, which is parallel to the reference axis CC. The air flow direction 290 is, accordingly, parallel to the end portions 258 and the surfaces 260 of the cooling fins 246. This relation between the air flow direction 290 and the cooling fins 246 allows air generated by the rotating first circulating fin 119 to pass over the surfaces 260 of the cooling fins 246 with little resistance. In addition, this air flow direction 290 relative to the cooling fins 246 reduces any eddy currents that may, in turn, reduce the air flow through the heat sink 200. In addition, as described above, the cooling fins 246 are thin enough to minimize air resistance, but thick enough to transfer heat from the core 210. Thus, the cooling fins 246 cause little resistance to the air flow through the heat sink 200, which in turn, allows for the maximum convection of heat from the cooling fins 246 to the surrounding atmosphere. As described above, the cooling fins 246 may be small enough to minimize the air barrier layer present on their surfaces, which in turn increases the cooling capability of the cooling device 100.

The thin cooling fins 246 and their placement relative to each other allow them to be condensed or "nested" which in turn allows a greater number of cooling fins 246 to convect heat to the surrounding atmosphere. In addition, the placement of the fin rings 240 and the cooling fins 246 create channels for air to flows past the cooling fins 246. One such channel is defined by the reference axis CC, which is parallel to the air flow direction 290. Other channels are parallel to the channel defined by the reference axis CC and other channels bisect the channel defined by the reference axis CC.

Referring again to FIG. 6, having described the cooling device 100, it will now be described cooling a heat generating device 330 that is mounted to a top surface 342 of a printed circuit board 340. The heat generating device 330 is described herein as being an integrated circuit that generates heat when it is in use. The heat generating device 330 may have a top surface 332 wherein most of the heat generated by the heat generating device 330 flows from the top surface 332 in a direction 334. The cooling device 100 may be operatively associated with the heat generating device 330 so that the lower portion 216 of the core 210 is in thermal contact with the top surface 332 of the heat generating device 330. In order to assure thermal conductivity between the heat generating device 330 and the cooling device 100, the cooling device 100 may be attached to the printed circuit board 340 in a conventional manner so as to bias the cooling device 100 onto the heat generating device 330.

When the heat generating device 330 is in use, it generates more heat than it can dissipate alone. Heat accumulates in the top surface 332 of the heat generating device 330 and generally flows in the direction 334. The heat generated by the heat generating device 330 is absorbed into the core 210 by virtue of the thermal contact between the top surface 332 of the heat generating device 330 and the lower portion 216 of the core 210. Thus, the temperature of the heat generating device 330 is reduced by the absorption of heat into the core 210. The heat absorbed by the core 210 dissipates to the surface 212 where some of the heat is convected directly to the surrounding atmosphere. The interference fits between the fin rings 240 and the core 210 cause the majority of the heat dissipated to the surface 212 of the core 210 to transfer to the fin rings 240 and into the cooling fins 246.

Simultaneous to heat being absorbed into the core 210 and dissipated to the cooling fins 246, the fan 110 forces air to flow in the air flow direction 290 past the surfaces 260 of the cooling fins 246. More specifically, the fan 110 may draw air into the cooling device 100 along an air flow direction 360. The air passes through the heat sink 200 in the air flow direction 290 and is exhausted along an air flow direction 362. Accordingly, the heat in the cooling fins 246 is convected into the surrounding atmosphere. As described above, the tapered portion 218 of the core 210 enables the air to flow freely from the heat sink 200, which in turn increases the amount of air that can be forced through the heat sink 200.

The rate of heat transfer between the core 210 and the cooling fins 246 is proportional to the temperature difference between the cooling fins 246 and the surface 212 of the core 210. Likewise, the heat transfer from the heat generating device 330 to the core 210 is proportional to the temperature of the core 210. Accordingly, a higher rate of heat transfer from the heat generating device 330 can be accomplished by significantly cooling the cooling fins 246. The temperature of the cooling fins 246 is proportional to their position relative to the heat generating device 330, wherein the cooling fins 246 positioned close to the heat generating device 330 are hotter than those positioned further from the heat generating device 330. By forcing relatively cool air in the air flow direction 290, all the cooling fins 246 are exposed to relatively cool air, which reduces their temperature. The relatively cool cooling fins 246 are, thus, able to transfer heat from the surface 212 of the core 210 at a high rate, which in turn, cools the core 210 at a high rate. The cooler core 210 is then able to remove a great amount of heat at a high rate from the heat generating device 330.

Due to inherent air restrictions in the heat sink 200 caused by the cooling fins 246, not all the air forced into the heat sink 200 by the fan 110 passes by the cooling fins 246. For example, the fan 110 may cause air pressure to build up in the cooling fins 246, which in turn, causes some air to leave the heat sink 200 without passing by all the fin rings 240. The heat sink 200 of FIG. 6 shows that some air may follow an air flow direction 370 and may be exhausted from the heat sink 200 without passing by all of the cooling fins 246. Accordingly, the air following the air flow direction 370 may not be used efficiently.

Figure 9:
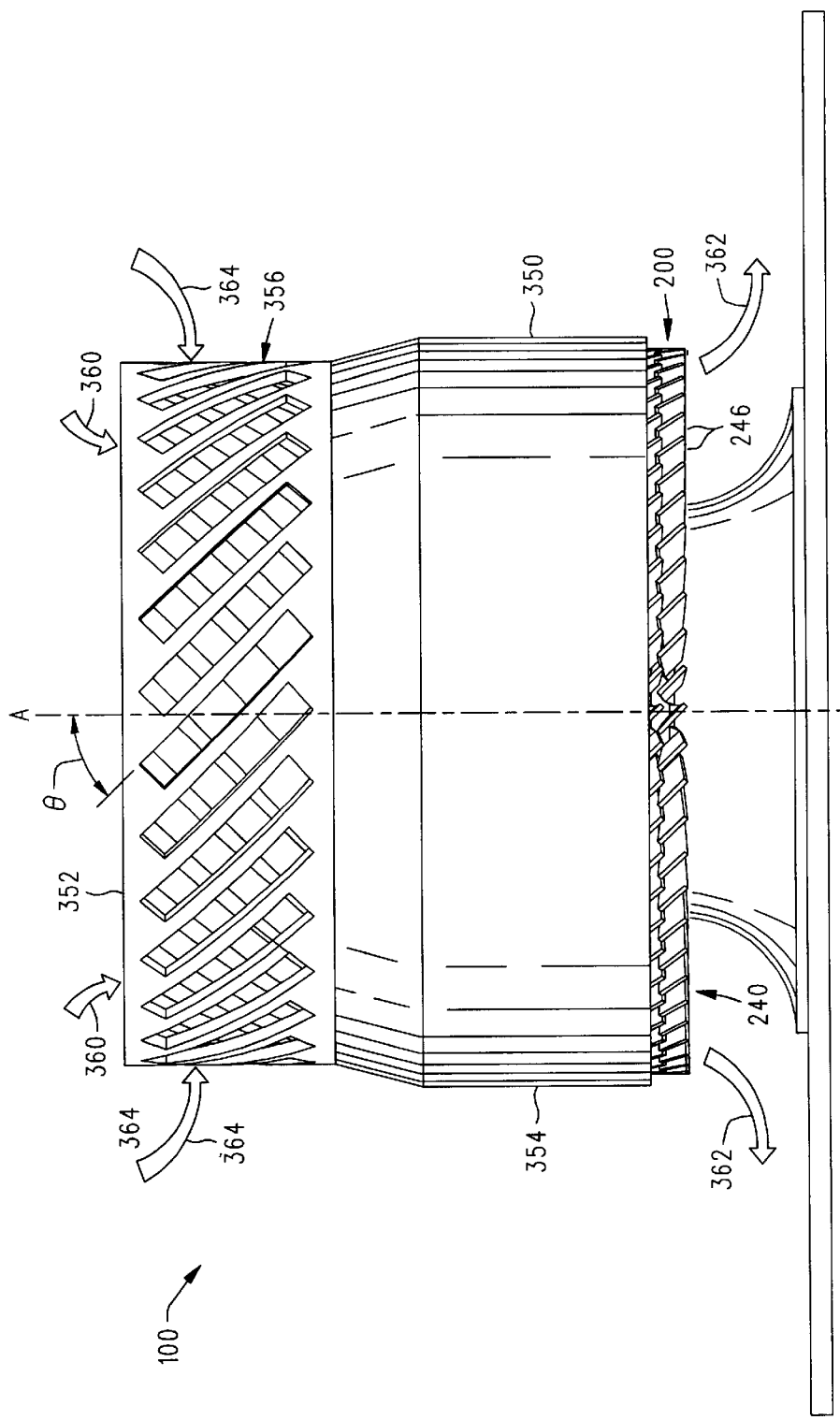
FIG. 9 is a side view of the cooling device of FIG. 6 with a shroud attached thereto.

Referring to FIG. 9, in order to assure all the air drawn into the cooling device 100 passes the cooling fins 246, a shroud 350 may be added to the cooling device 100. The shroud 350 may, as an example, be a duct that fits over the heat sink 200 and does not allow air to escape from the heat sink 200 until it has passed by all the cooling fins 246. Thus, all the air entering the cooling device 100 along the air flow direction 360 is exhausted from the cooling device 100 along the air flow direction 362.

The shroud 350 may have an upper portion 352 and a lower portion 354. The upper portion 352 may substantially encompass the fan, not shown in FIG. 9, and the lower portion 354 may substantially encompass the heat sink 200. A plurality of openings 356 may be formed into the upper portion 352 in order to facilitate air flow through the cooling device 100. More specifically, air may flow in an air flow direction 364 through the openings 356 where it joins the air flowing along the air flow direction 360. Accordingly, the openings 356 may serve to increase the volume of air that passes the cooling fins 246, which in turn increases the convection of heat to the surrounding atmosphere. The shroud 350 is illustrated as having slot-shaped openings 364 that are slanted to correlate with the angle of the first circulating fin 119, FIG. 6. The openings 364 described herein are positioned at the angle θ relative to the reference axis AA, which in the embodiment described herein is forty-five degrees.

Having described an embodiment of the cooling device 100, other embodiments of the cooling device 100 will now be described.

Referring again to FIG. 5, the cooling device 100 has been described here as having the fin rings 240 pressed onto the core 210. Pressing the fin rings 240 onto the core 210 creates interference fits between the fin rings 240 and the core 210, which provide for high thermal conductivity between the core 210 and the fin rings 240. The interference fits, however, require that the core 210 and the fin rings 240 be manufactured to precise specifications. If precise manufacturing specifications are not achieved, the fin rings 240 may be loose on the core 210 or the fin rings 240 may not be able to be pressed onto the core 210.

Figure 10:
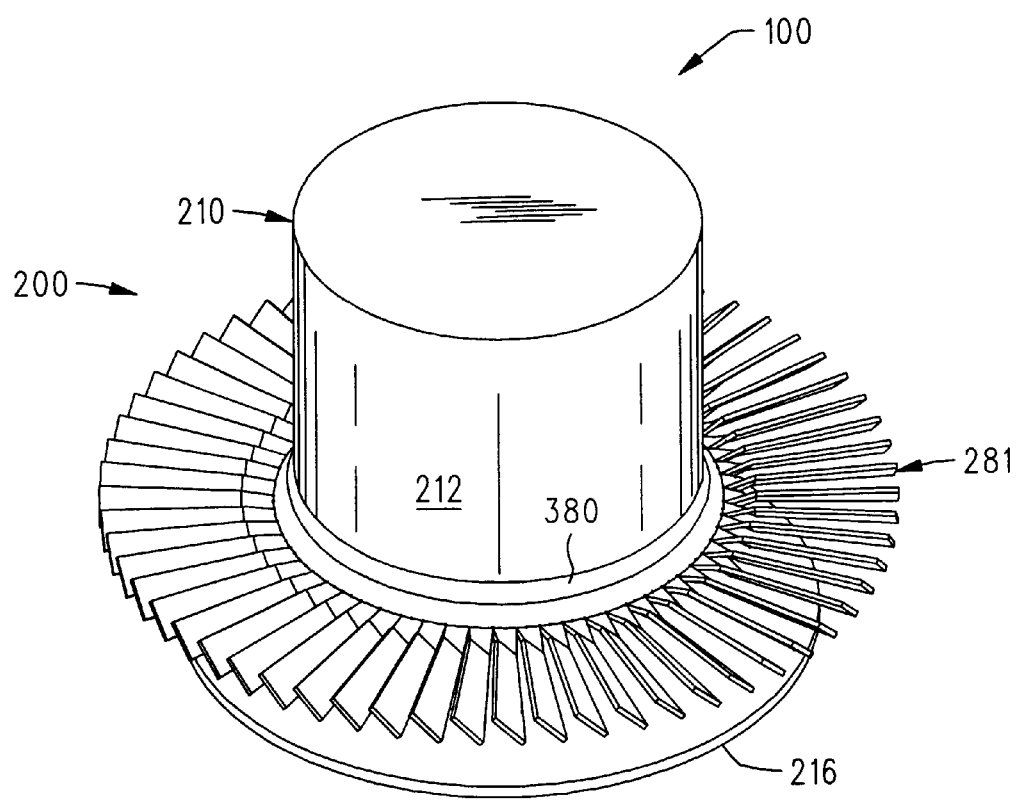
FIG. 10 is a top perspective view of the cooling device of FIG. 2 with the addition of a compression ring.

Referring to FIG. 10, the above-described problems of controlling the specifications of the fin rings 240, FIG. 6, may be overcome by the addition of compression rings partially encompassing the core 210. In this embodiment of the heat sink 200, interference fits between the fin rings 240 and the core 210 are not required. A compression ring 380 may abut the top side of the first fin ring 281. A second compression ring, not shown, may abut the bottom side of the first fin ring 281. The compression ring 380 may be a ring of thermally conductive material, such as copper or aluminum, that is pressed onto the core 210 and firmly abuts the first fin ring 281. Heat in the core 210 may then be transferred to the first fin ring 281 via the compression ring 380. Accordingly, the use of the compression ring 380 permits the first fin ring 281 to be manufactured to looser specifications than those described above. In one embodiment, the compression rings form interference fits with the fin rings and the core when they are pressed together. For example, the compression rings may distort to form the interference fits.

A plurality of compression rings may be pressed or otherwise placed onto the core 210 during the manufacturing process of the heat sink 200. For example, one compression ring, not shown in FIG. 10, may be pressed onto the core 210 in the vicinity of the lower portion 216. The first fin ring 281 may then be placed over the core 210 so as to abut the compression ring located in the vicinity of the lower portion 216. The compression ring 380 may then be pressed onto the core 210 so as to abut the first fin ring 281. Accordingly, the first fin ring 281 is sandwiched between compression rings. The compression rings may then be forced together to so that the first fin ring 281 is tightly compressed between them. This compression serves to enhance the thermal conductivity between the compression rings and the first fin ring 281, which in turn enhances the cooling capability of the heat sink 200.

Figure 11:
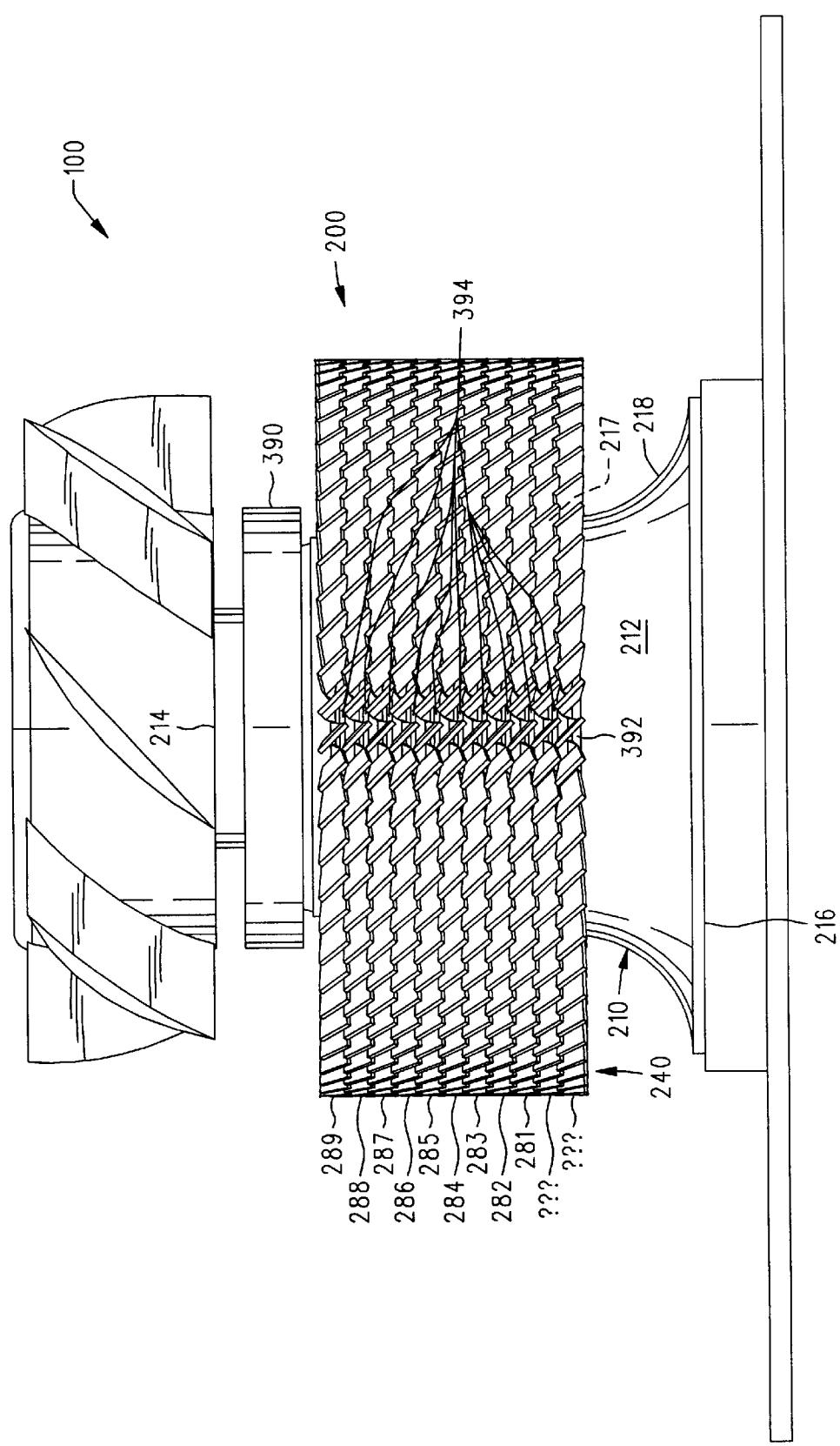
FIG. 11 is a side view of the cooling device of FIG. 1 with a plurality of compression rings attached thereto.

Referring to FIG. 11, a plurality of compression rings may be pressed onto the core 210. The heat sink 200 illustrated in FIG. 11 is similar to the heat sink 200 illustrated in FIG. 6, however, the heat sink 200 of FIG. 11 has a plurality of compression rings placed or otherwise pressed onto the core 210. The heat sink 200 may have a top compression ring 390 located in the vicinity of the top portion 214 of the core 210. The heat sink 200 may also have a bottom compression ring 392 located in the vicinity of the junction of the cylindrical portion 217 and the tapered portion 218 of the core 210. A plurality of inner compression rings 394 may be pressed onto the core 210, wherein one of the plurality of inner compression rings 394 is located between each of the fin rings 240.

The heat sink 200 of FIG. 11 may be manufactured by first pressing the bottom compression ring 392 onto the core 210.

The first fin ring 281 may then be slipped over the core 210 and placed near the bottom compression ring 392. An inner compression ring 394 may then be pressed onto the core so as to sandwich the first fin ring 281 between compression rings. The second fin ring 282 may then be slipped over the core 210 to abut the previously pressed on inner compression ring 394. The process of alternating fin rings 240 and inner compression rings 394 continues until all of the fin rings 240 have been placed onto the core 210. Accordingly, an inner compression ring 394 is located between each fin ring 240. The top compression ring 390 may then be pressed onto the core 210. In order to assure that thermal contact exists between the fin rings 240 and the compression rings 390, 392, 394, the top compression ring 390 and the bottom compression ring 392 may be pressed together. This will cause the fin rings 240 to contact all the compression rings 390, 392, 394, which increases the thermal conductivity between the surface 212 of the core 210 and the fin rings 240.

Referring again to FIG. 6, in one embodiment of the cooling device 100, the core 210 may be a heat pipe or have a heat pipe located therein. A heat pipe is a device that is known in the art and serves to rapidly transfer heat. Thus, the interior of the core 210 may be a partially evacuated chamber containing a small amount of a liquid. When the core 210 is cool, the liquid is located in the vicinity of the lower portion 216 of the core 210. The liquid evaporates when it is heated by the heat generating device 330. The vapor from the evaporated liquid condenses on the sides of the core 210 and, thus, transfers its heat to the sides of the core 210. The heat may then quickly transfer to the surface 212 of the core 210. The heat may then be convected to the surrounding atmosphere as described above. The use of the heat pipe substantially increases the heat transfer through the core 210, which in turn increases the cooling capability of the cooling device 100. Examples of heat pipes are disclosed in the following United States patents and patent applications, which are all hereby incorporated by reference for all that is disclosed therein: Ser. No. 09/376,627 of Wagner et al. for COOLING APPARATUS FOR ELECTRONIC DEVICES; registration number U.S. Pat. No. 5,694,295 of Masataka et al. for HEAT PIPE AND PROCESS FOR MANUFACTURING THE SAME.

The heat sink 200 has been described herein as having a plurality of cooling fins 246 that extend radially from the core 210. Other embodiments of the heat sink 200 have different cooling fin configurations as described in greater detail below.

Figure 12:
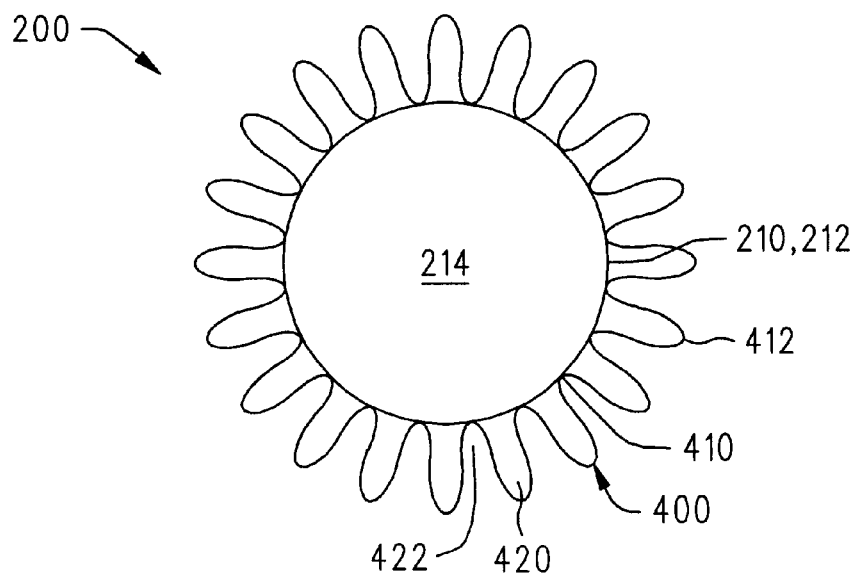
FIG. 12 is a top cutaway view of a cooling device having a ribbon-type cooling fin associated therewith.

One embodiment of a fin configuration is illustrated in FIG. 12 and uses a ribbon-type cooling fin, which is sometimes referred to herein as a cooling ribbon 400. The cooling ribbon 400 may, as an example, be constructed from a single piece of a thermally conductive material, such as a sheet of copper or aluminum. Alternatively, the cooling ribbon 400 may be extruded in a conventional manner. The cooling ribbon 400 may have a plurality of contact portions 410 and end portions 412. The contact portions 410 may serve to contact the surface 212 of the core 210 and may, thus, be points where heat is transferred from the core 210 into the cooling ribbon 400. The end portions 412 may be portions of the cooling ribbon 400 that are located furthest from the surface 212 of the core 210. A plurality of inner air channels 420 may be located between the surface 212 of the core 210 and the end portions 412. A plurality of outer air channels 422 may be located between the contact portions 410 and the cooling ribbon 400.

The cooling ribbon 400 may be pressed onto the core 210. For example, in one embodiment of the heat sink 200, a single cooling ribbon 400 is pressed onto the core 210 and extends at least a portion of the length of the cylindrical portion 217, FIG. 3 of the core 210. In another embodiment of the heat sink 200, a plurality of cooling ribbons 400 are pressed onto the heat sink 200 and extend at least a portion of the length of the cylindrical portion 217 of the core 210. Heat in the surface 212 of the core 210 transfers to the cooling ribbon 400 via the contact portions 410. The heat is then convected into the surrounding atmosphere. An air blowing device, such as a fan or duct work, not shown in FIG. 12, may force air in the inner air channel 420 and the outer air channel 422 to increase the convection of the heat in the inner air channel 420 to the surrounding atmosphere.

Figure 13:
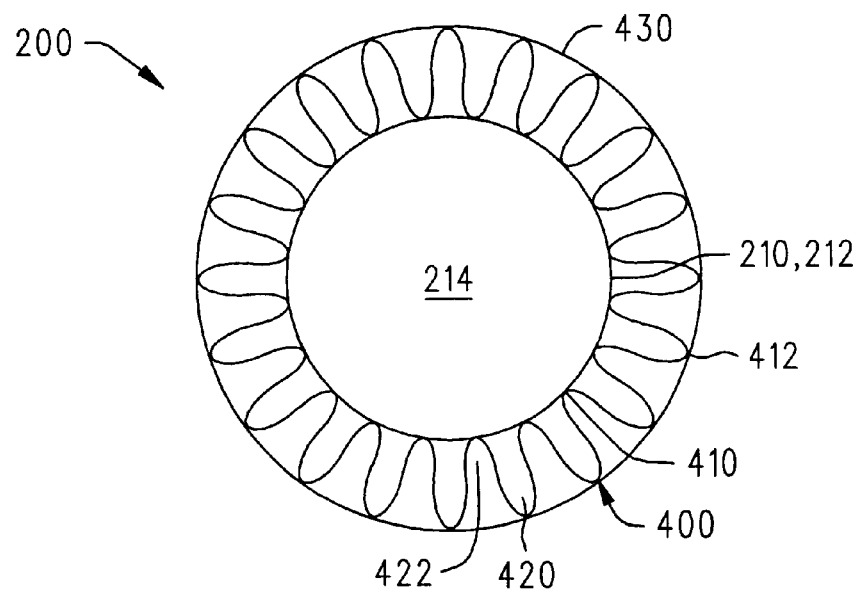
FIG. 13 is the cooling device of FIG. 12 with the addition of a shroud encompassing the core and ribbon-type cooling fin.

Referring to FIG. 13, as with other embodiments of the heat sink 200, a shroud 430 may be placed over the heat sink 200. The shroud 430, in conjunction with an air blowing device, forces air in the outer air channel 422 to remain in the outer air channel 422 throughout the length of the shroud 430. Accordingly, air in the outer air channel 422 is used more efficiently, which improves the overall efficiency of the cooling device 100.

Figure 14:
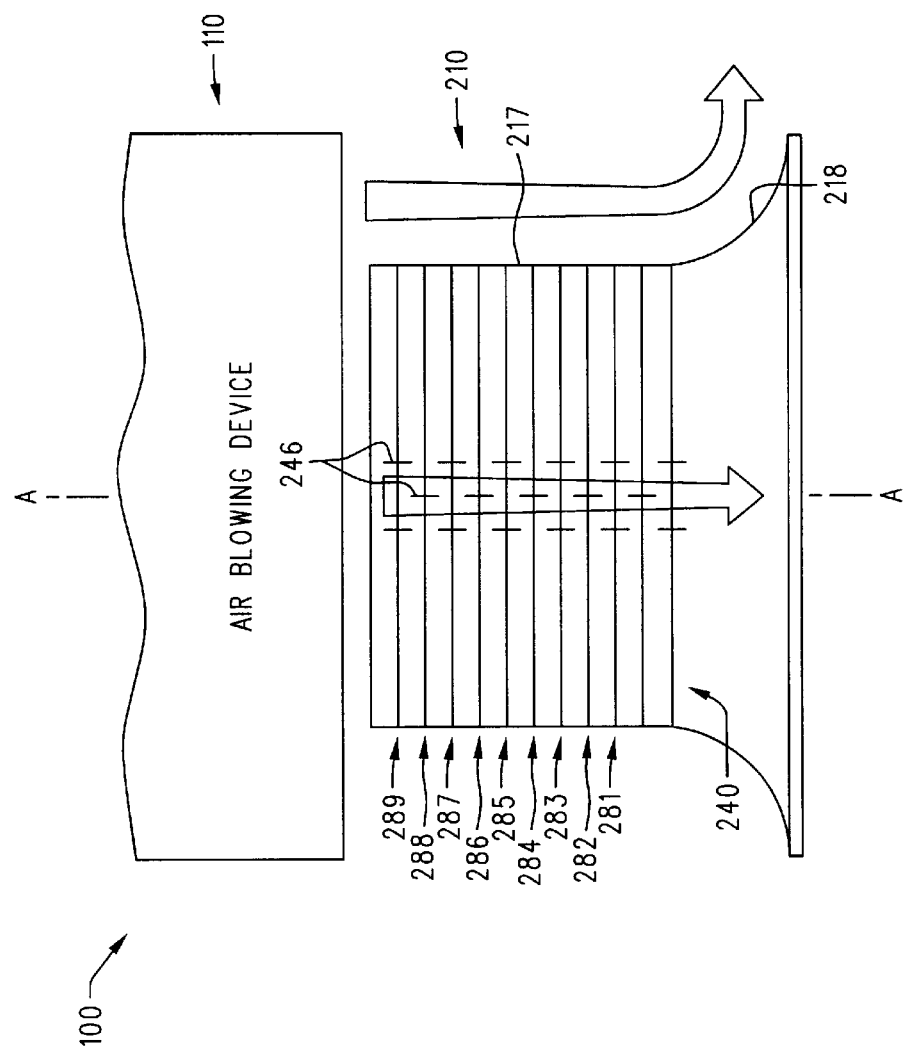
FIG. 14 is a side, schematic illustration of a cooling device having cooling fins extending parallel to the core.

Referring to FIG. 14, in another embodiment of the heat sink 200, the cooling fins 246 extend axially along the length of the core 210 similar to the ribbon-type cooling fin 400 of FIG. 12. More specifically, the cooling fins 246 may extend substantially parallel to the reference axis AA. This cooling fin configuration may be used when the air flow from the air blowing device 110 extends substantially parallel to the reference axis AA. For example, in the embodiment where the air blowing device 110 is duct work, the airflow generated by the air blowing device 110 will likely extend along the reference axis AA as shown in FIG. 14. Thus, the benefits of having the cooling fins 246 parallel to the air flow as described above are maintained.

The cooling fins 246 shown in FIG. 14 and the cylindrical portion 217 of the core 210 may be extruded as a single piece. Accordingly, heat transfer between the core 210 and the cooling fins 246 is may be improved. As with the other embodiments of the cooling device 100, a shroud, not shown in FIG. 14, may substantially encompass the core 210 and the cooling fins 246.

Figure 15:
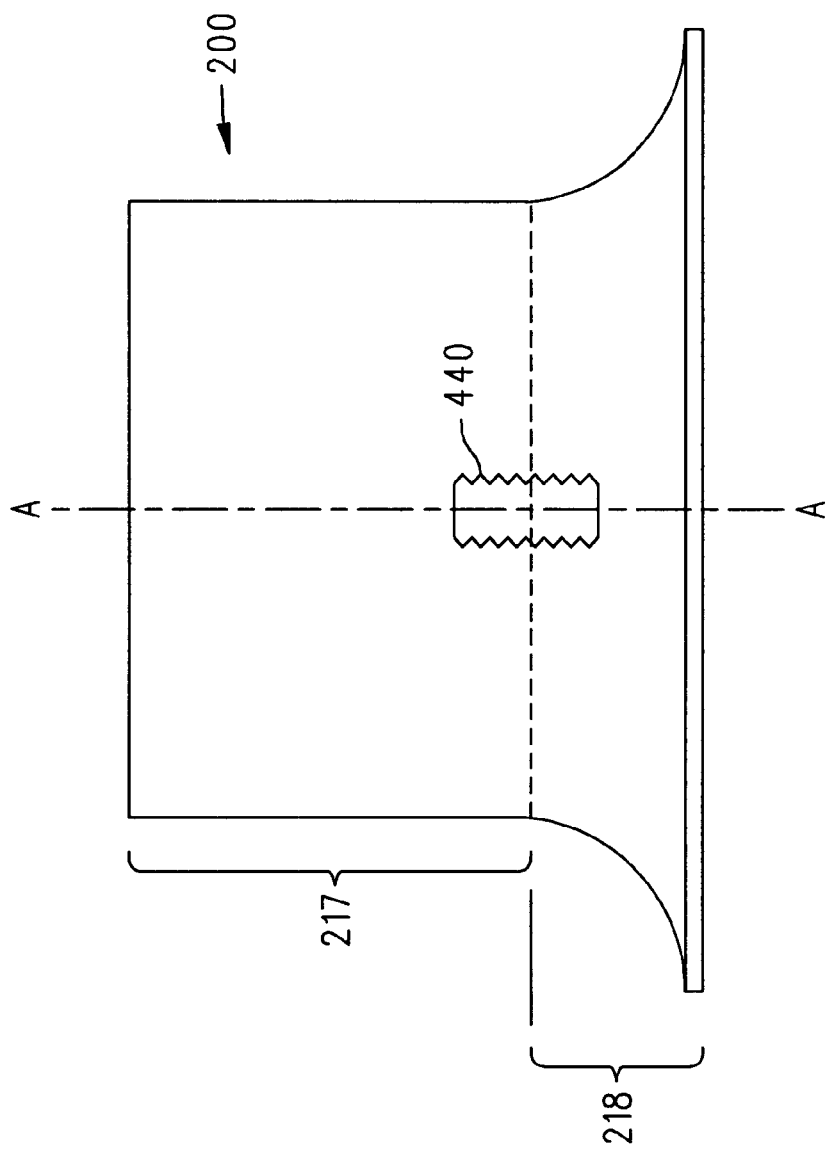
FIG. 15 is a side view of an embodiment of the core member of FIG. 3 being constructed from two components.
Figure 16:
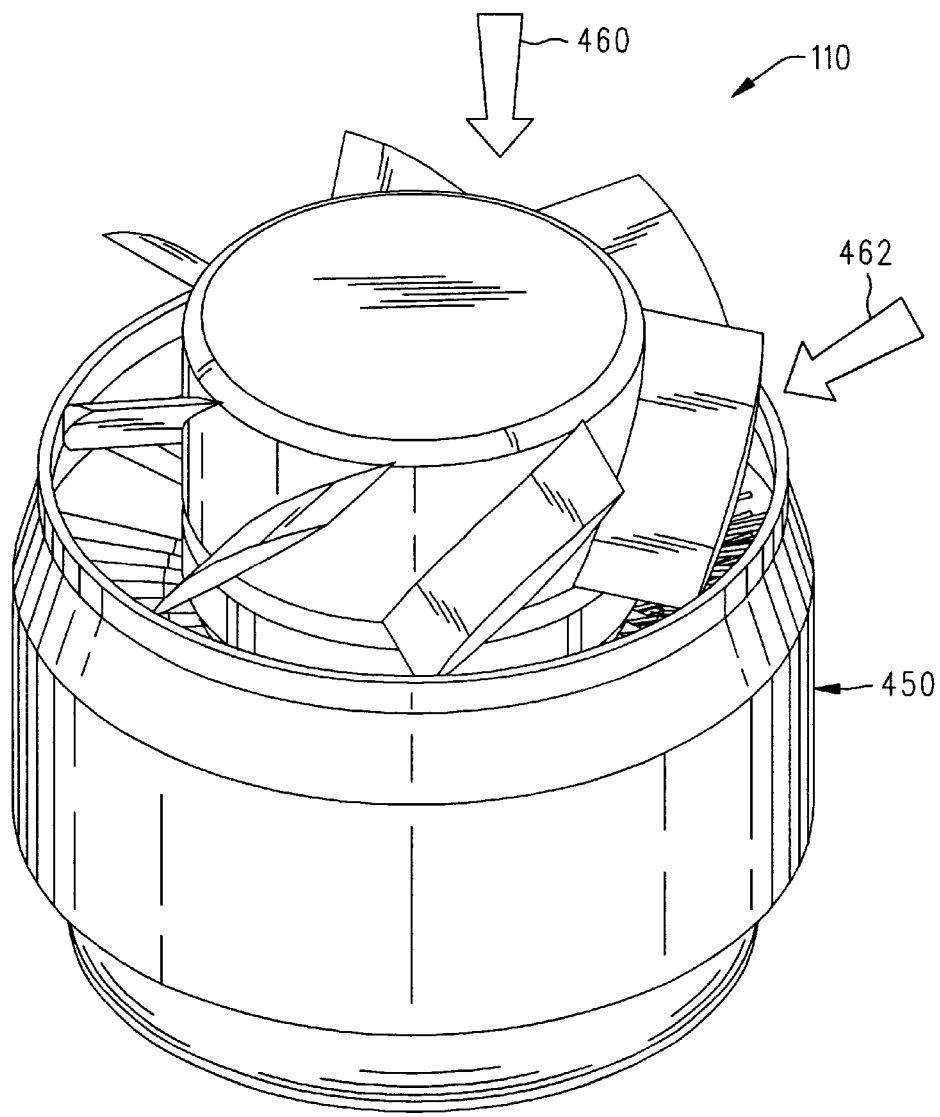
FIG. 16 is a side view of a cooling device having a reduced shroud.

The cores 210 of the heat sinks 200 described above may alternatively be constructed from two pieces of material as shown in FIG. 15. The cylindrical portion 217 may be manufactured separate from the tapered portion 218. The two portions may then be assembled so as to provide thermal contact therebetween. In the embodiment shown in FIG. 15 a screw 440 is used to attach the tapered portion 218 to the cylindrical portion 217. It should be noted that other attaching mechanisms, such as the use of an adhesive may be used to attach the two portions together. In another embodiment, a heat conductive compound may be located between the cylindrical portion and the tapered portion 218 in order to improve the thermal conductivity between the two portions.

The embodiment of the core 210 shown in FIG. 15 facilitates manufacturing the core 210 and any cooling fins that may be attached thereto by extrusion. With additional reference to FIGS. 12 and 14, any of the embodiments of the heat sink 200 having cooling fins that extend along the reference axis AA may be extruded from the same piece of material as the core 210. The extruded core and cooling fin combination may be cut to an appropriate size. The tapered portion 218 may then be added to the combination to form the heat sink 200.

Referring again to FIG. 6, the fin rings 240 have been described as being adjacent to the surface 212 of the core 210. It is to be understood that the fin rings 240 may be attached to the core by numerous methods. For example, the fin rings 240 may be pressed onto the core 210. In another example, the core fin rings 240 may be soldered or brazed to the core 210.

Another embodiment of a shroud 450 is shown in FIG. 15. As shown in FIG. 15, the shroud 450 does not extend the full length of the fan 110. This embodiment of the shroud 450 may increase air flow by causing air to enter the cooling device 100 by way of an airflow 460 and an airflow 462.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A heat sink for removing heat from a heat source, said heat sink comprising:
   a core member comprising at least one core member first surface, said at least one first surface being adapted to contact at least a portion of said heat source;
   at least one outer peripheral surface located on said core member, at least a portion of said at least one outer peripheral surface being tapered, wherein the circumference of said at least one outer peripheral surface in the proximity of said first surface being greater than the circumference of said at least one outer peripheral surface not in the proximity of said first surface;
   at least one cooling fin operatively connected to said at least one outer peripheral surface, said at least one cooling fin extending in a direction substantially normal to said at least one core member first surface; and
   a shroud having at least one inner surface, wherein said at least one inner surface is located adjacent said at least one cooling fin, wherein said shroud has a first portion and a second portion, wherein said first portion is located adjacent said at least one cooling fin, wherein said second portion extends beyond said core member, and wherein said second portion has at least one slot formed therein.

2. The heat sink of claim 1, wherein the circumference of said at least one outer peripheral surface is greatest at a junction of said at least one outer peripheral surface and said at least one first surface.

3. The heat sink of claim 1, wherein said at least a portion of said at least one outer peripheral surface being tapered forms a continuous surface.

4. The heat sink of claim 1, wherein said at least one cooling fin provides at least one air channel, and said at least one air channel being adjacent said at least one cooling fin.

5. The heat sink of claim 4, and further comprising at least one second cooling fin, wherein said at least one second cooling fin bisects said at least one air channel.

6. The heat sink of claim 1, and further comprising a cooling fin device comprising a collar member, wherein said at least one cooling fin is attached to said collar member, said cooling fin device being in thermal contact with said at least one outer peripheral surface.

7. The heat sink of claim 6, wherein an interference fit exists between said at least one outer peripheral surface of said core member and said cooling fin device.

8. The heat sink of claim 1, wherein said core member comprises a heat pipe.

9. The heat sink of claim 1, wherein said core member further comprises a core member second surface oppositely disposed said at least one first surface, and wherein said heat sink further comprises an air blowing device located in the vicinity of said core member second surface.

10. The heat sink of claim 9, wherein said air blowing device has an air path associated therewith, and wherein said air path is extends in a direction between said at least one core member first surface and said core member second surface.

11. The heat sink of claim 1, wherein said at least one cooling fin has a first end and a second end, wherein both said first end and said second end are adjacent said at least one outer peripheral surface of said core member.

12. The heat sink of claim 1, wherein said core member comprises a core first portion and a core second portion being in thermal contact, said core first portion comprising the portion of said at least one outer peripheral surface being tapered.

13. The heat sink of claim 12, wherein said core second portion and said at least one cooling fin are formed from a single piece of material.

14. The heat sink of claim 12, wherein said core second portion and said at least one cooling fin are extruded.

15. A heat sink for removing heat from a heat source, said heat sink comprising:
   a core member comprising at least one core member first surface, said at least one first surface being adapted to contact at least a portion of said heat source;
   at least one outer peripheral surface located on said core member; and
   at least one cooling fin operatively connected to said at least one outer peripheral surface, said at least one cooling fin extending in a direction substantially normal to said at least one core member first surface;
   at least a portion of said at least one outer peripheral surface being tapered, wherein the circumference of said at least one outer peripheral surface in the proximity of said first surface being greater than the circumference of said at least one outer peripheral surface not in the proximity of said first surface, wherein said at least a portion of said core member and said at least one cooling fin are extruded from a single piece of material.

16. The heat sink of claim 15, wherein the circumference of said at least one outer peripheral surface is greatest at a junction of said at least one outer peripheral surface and said at least one first surface.

17. The heat sink of claim 15, wherein said at least a portion of said at least one outer peripheral surface being tapered forms a continuous surface.

18. The heat sink of claim 15, wherein said at least one cooling fin provides at least one air channel, and said at least one air channel being adjacent said at least one cooling fin.

19. The heat sink of claim 18, and further comprising at least one second cooling fin, wherein said at least one second cooling fin bisects said at least one air channel.

20. The heat sink of claim 15, and further comprising a cooling fin device comprising a collar member, wherein said at least one cooling fin is attached to said collar member, said cooling fin device being in thermal contact with said at least one outer peripheral surface.

21. The heat sink of claim 20, wherein an interference fit exists between said at least one outer peripheral surface of said core member and said cooling fin device.

22. The heat sink of claim 15, wherein said core member comprises a heat pipe.

23. The heat sink of claim 15, wherein said core member further comprises a core member second surface oppositely disposed said at least one first surface, and wherein said heat sink further comprises an air blowing device located in the vicinity of said core member second surface.

24. The heat sink of claim 23, wherein said air blowing device has an air path associated therewith, and wherein said air path is extends in a direction between said at least one core member first surface and said core member second surface.

25. The heat sink of claim 15, wherein said at least one cooling fin has a first end and a second end, wherein both said first end and said second end are adjacent said at least one outer peripheral surface of said core member.

26. The heat sink of claim 15, wherein said core member comprises a core first portion and a core second portion being in thermal contact, said core first portion comprising the portion of said at least one outer peripheral surface being tapered.

27. The heat sink of claim 26, wherein said core second portion and said at least one cooling fin are formed from a single piece of material.

28. The heat sink of claim 26, wherein said core second portion and said at least one cooling fin are extruded.

* * * * *